United States Patent [19]

Beineke

[11] Plant 4,543

[45] Jun. 10, 1980

[54] DISTINCT VARIETY OF BLACK WALNUT TREE

[75] Inventor: Walter F. Beineke, West Lafayette, Ind.

[73] Assignee: Purdue Research Foundation, West Lafayette, Ind.

[21] Appl. No.: 939,835

[22] Filed: Sep. 5, 1978

[51] Int. Cl.[2] ..... A01H 5/00

[52] U.S. Cl. ..... Plt./32

[58] Field of Search ..... Plt./32

*Primary Examiner*—Robert E. Bagwill
*Assistant Examiner*—James R. Feyrer
*Attorney, Agent, or Firm*—John R. Nesbitt

[57] ABSTRACT

A new and distinct cultivar of black walnut tree (*Juglans nigra L.*) which is distinctly characterized by rapid growth rate, strong central stem tendency, average time in leafing, and outstanding straightness (little sweep and few crooks) thereby producing excellent timber qualities. The new variety has outstanding nut qualities as well such as abundant annual crops of large-sized nuts, begins nut-bearing early in life of tree, average 3 nuts per cluster, and produces kernels which exceed 20 percent of nut weight. The nuts are large and ripen early. The pistillate flowers mature early while pollen maturity is mid-season. In most years there is some overlap in female and male flowering. Flowering begins very early in the life of the tree. This new variety of black walnut tree was discovered by the applicant near Darlington, Ind. on land owned by Purdue University in a cultivated area. It occurred as a wild tree growing on land managed for timber-growing purposes and was discovered in the course of a search for unique and high quality black walnut trees to be utilized in breeding for outstanding timber qualities. This selection has been designated as BW55 in records maintained on the performance of grafts made from the original selection and will be known henceforth as "Purdue 1".

5 Drawing Figures

BACKGROUND OF THE INVENTION

Figure 2:
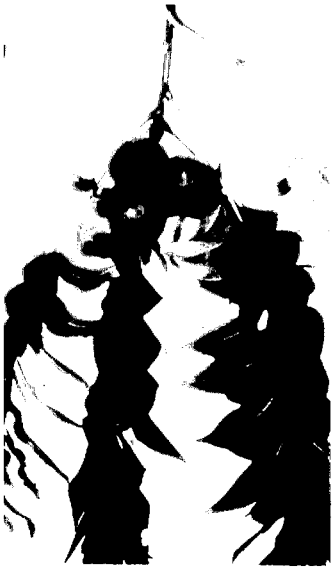
FIG. 2 is a photograph showing a twig with leaves and nuts attached from Purdue 1.
Figure 1:
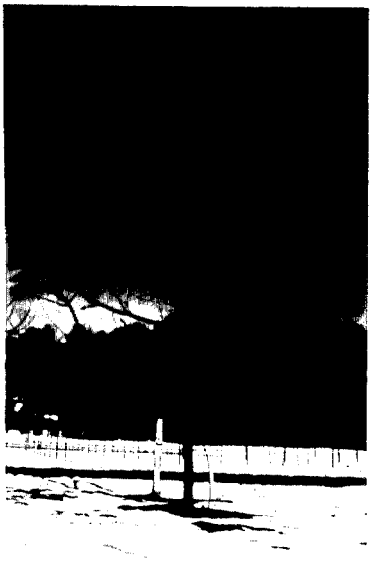
FIG. 1 is a photograph showing the timber form of Purdue 1.
Figure 3:
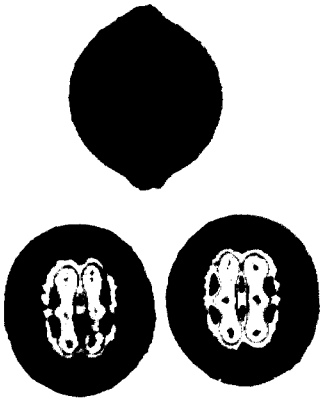
FIG. 3 is a photograph showing a cross-section view of the nut and hull in Purdue 1.
Figure 4:
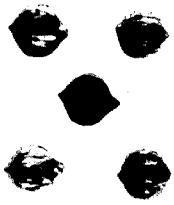
FIG. 4 is a photograph showing the nuts with hull removed.
Figure 5:
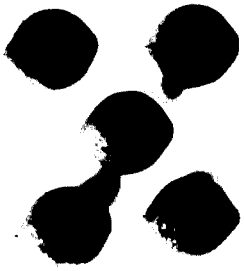
FIG. 5 is a photograph showing the nuts with hull intact.

After the original clone was selected, and assigned an identity number of BW55, the aforesaid tree was reproduced by collecting scions from it and grafting these onto common black walnut rootstocks at Martell Forest, Purdue University. These asexual reproductions ran true to the parent tree and to each other in all respects.

DETAILED DESCRIPTION OF THE NEW VARIETY

The botanical details of this new and distinct variety of walnut tree are as follows:

Tree:

*Size.*—Large.

*Vigor.*—Vigorous.

*Growth rate.*—Rapid growth — 20% larger in diameter than average, 14% taller than average, and 38% more cubic foot volume than average at 8 years of 22 clones.

*Form.*—Excellent timber form — 53% straighter than average. Fewest crooks of 80 clones. Strong central stem tendency and pyramid-shaped crown development.

Trunk:

*Bark.*—Dark brown to gray.

*Texture.*—Interlacing ridges.

Branches:

*Diameter.*—Average.

*Length.*—Average.

*Branch angle.*—Lower branches — 61% average.

*Foliage.*—Quantity — abundant. Density — heavy.

Leaves:

*Compound leaves.*—Size — shorter than average; average length 14½".

*Leaflets.*—Size — large; average length — 4⅜"; average width — 1½". Shape — lanceolate; acutely pointed. Thickness — thin; texture — smooth; margin — serrated; petiole — short; color — topside — dark green; underside — light green.

*Anthracnose resistance.*—Fair to good resistance.

*Time of leafing.*—Early — averages 5 days earlier or 45% earlier than average.

Flowering habit:

*Age at which tree starts producing catkins.*—Very early.

*Number of catkins produced.*—Abundant.

*Size of catkins.*—Average.

*Time of Pollen shed.*—Mid-season.

*Age at which time tree starts producing pistillate flowers.*—Very early.

*Number of pistillate flowers produced by young tree.*—Abundant.

*Number of pistillate flowers produced by mature tree.*—Abundant.

*Lateral shoots producing pistillate flowers.*—Abundant some years.

*Number of pistillate flowers per inflorescence.*—Average 3.

*Timing of pistillate flower receptivity.*—Very early.

*Coincidence of staminate and pistillate bloom.*—Usually a slight overlap.

Nut crop:

*Bearing.*—Annual.

*Productivity.*—Heavy.

*Ripening period.*—Early.

*Evenness of maturity (period between first and last nuts are ready for harvest).*—Medium.

*Quality.*—Very good.

*Distribution of nuts on tree.*—Well distributed throughout tree.

Hull:

*Outer surface.*—Warty.

*Form.*—Pointed both ends, flattened in suture plane.

*Thickness.*—Medium.

*Size.*—Large; average length — 2½"; average diameter in suture plane — 1⅞"; average diameter cheek to cheek — 2 1/16".

Nut:

*Size.*—Large; average length — 1¾"; average diameter in suture plane — 1⅛".

*Uniformity of size.*—Some variation.

*Form.*—Oblong, flattened in suture plane.

*Blossom end.*—Pointed.

*Basal end.*—Pointed.

*Weight.*—Dry weight of ten nuts — 170.0 gm; dry weight of ten kernels — 34.4 gm.; average percentage kernel to nut — 20.2%.

*Thickness of shell.*—Medium.

*Fill.*—Good.

Kernel:

*Size.*—Large.

*Plumpness.*—Plump.

*Shrivel.*—None.

*Flavor.*—Good.

*Color.*—Light.

The walnut tree and its nuts herein described may vary in slight detail due to climatic and soil conditions under which the variety may be grown; the present description being of the variety as grown near West Lafayette, Ind.

What is claimed is:

1. A new and distinct variety of black walnut tree substantially as illustrated and described, which has excellent timber quality, is fast growing, has strong central stem tendency, little sweep, few crooks; earlier than average in time of leafing, pistillate flowers early, pollen sheds mid-season, produces abundant annual crops of large-size nuts; averages 3 per cluster, the percentage of weight of kernel to nut approximately on the average 20 percent; nut bearing begins early in life of tree.

* * * * *